(12) United States Patent
Zhong et al.

(10) Patent No.: US 8,221,801 B2
(45) Date of Patent: Jul. 17, 2012

(54) ANTIVIRAL PRODUCT

(75) Inventors: Shouming Zhong, Oxford (GB);
Hongwen Yu, Oxford (GB)

(73) Assignee: Phynova Limited, Long Hangborough, Oxon (GB)

( * ) Notice: Subject to any disclaimer, the term of this patent is extended or adjusted under 35 U.S.C. 154(b) by 433 days.

(21) Appl. No.: 12/304,893

(22) PCT Filed: Jun. 6, 2007

(86) PCT No.: PCT/GB2007/002078
§ 371 (c)(1),
(2), (4) Date: Mar. 9, 2010

(87) PCT Pub. No.: WO2007/144569
PCT Pub. Date: Dec. 21, 2007

(65) Prior Publication Data
US 2010/0158864 A1   Jun. 24, 2010

(30) Foreign Application Priority Data

Jun. 16, 2006 (GB) .................................. 0612025.7

(51) Int. Cl.
*A01N 65/00* (2009.01)
(52) U.S. Cl. ..................................................... 424/725
(58) Field of Classification Search ........................ None
See application file for complete search history.

(56) References Cited

U.S. PATENT DOCUMENTS

| 2005/0074428 A1 | 4/2005 | Ko |
| 2005/0147699 A1 | 7/2005 | Wu et al. |

FOREIGN PATENT DOCUMENTS

| CN | 1393255 A | 1/2003 |
| CN | 1448163 A | 10/2003 |
| CN | 1593586 A | 3/2005 |
| CN | 1607003 A | 4/2005 |
| CN | 1616097 A | 5/2005 |
| WO | 2004112720 A2 | 12/2004 |
| WO | 2005079823 A1 | 9/2005 |
| WO | 2007020382 A2 | 2/2007 |

OTHER PUBLICATIONS

Rios, J.L. and Waterman, P.G., A Review of the Pharmacology and Toxicology of Astragalus; Phytotherapy Research; Mar. 10, 1997; pp. 411-418; vol. 11; 1997 John Wiley & Sons, Ltd.

*Primary Examiner* — Michael Meller
(74) *Attorney, Agent, or Firm* — Dickinson Wright PLLC

(57) ABSTRACT

The present invention relates to a novel antiviral product, its use in the treatment of hepatitis C, and its process of manufacture. More particularly it relates to a characterized product exhibiting antiviral activity against Hepatitis C virus (HCV). In one embodiment there is provided a single herb *Astragalus* extract, or an active fraction thereof, for use as an antiviral in the treatment of hepatitis C.

9 Claims, 11 Drawing Sheets

** Fraction AS-C is the active fraction for PYN 18

UV254nm daylight

FIG. 11

UV254nm daylight

TLC

Developing system: chloroform: methanol: water (85:15:1)

Detection: Spray 10% surface acid in ethanol solution and heat the plate until the spot appeared. Observe the plate under daylight.

TLC

Developing system: chloroform: methanol: water (85:15:1)

Detection: at UV254nm or with iodine steam and heat the plate until the spots clearly appeared. Observe the plate under daylight.

TLC

Developing system: chloroform: methanol: water (85:15:1)

Detection: at UV254nm or with iodine steam and heat the plate until the spots clearly appeared. Observe the plate under daylight.

AS-C-I-2    AS-C-I-3

ANTIVIRAL PRODUCT

TECHNICAL FIELD OF THE INVENTION

The present invention relates to a novel antiviral product, its use in the treatment of hepatitis C, and its process of manufacture. More particularly it relates to a characterised product exhibiting antiviral activity against Hepatitis C virus (HCV). That the product exhibits activity in both a replicon test and particularly a polymerase test (NS5B) is suggestive of possible broader activity, against, for example, viruses within the Flaviviradae.

BACKGROUND OF THE INVENTION

Chronic infection with HCV is common, affecting up to 1% of the UK population, and the World Health Organisation (WHO) estimated that more than 200 million people globally are infected with HCV. It is well recognised that chronic HCV infection is associated with a wide variety of symptoms including fatigue, upper abdominal pain and dyspepsia, which lead to an overall reduction in the quality of life. Conventional therapy with pharmaceutical agents leads to the reduction of viral load but is effective in only about 40% of patients. There is thus a need for effective treatments that can reduce the symptoms associated with HCV infection and thereby improve the quality of life of a greater percentage of chronic hepatitis C (CHC) patients.

Furthermore there is a need for products that will target (and inhibit the activity of) the causative virus with less side effects.

In applicant's international application WO2005079823 there is disclosed a four herb combination product which in addition to providing symptomatic relief had been shown, by way of a replicon assay, to exhibit anti-HCV activity (inhibition of 41.8%) at a dilution of 1/350.

The product is composed of four herbal extracts and is formulated as follows:

Herbal Extracts:

| | |
|---|---|
| Milk Thistle Fruit dry extract | 0.200 g |
| Chinese Sage Root dry extract | 0.225 g |
| *Schisandra* Fruit dry extract | 0.400 g |
| *Astralagus* Root dry extract | 0.585 g |

Excipients:

| | |
|---|---|
| Macrogol 6000 powder | 0.600 g |
| Ferwogel 30.385 (molecular weight $3.5$-$4.0 \times 10^6$) | 0.070 g |
| Mannitol EZ | 0.160 g |
| Aerosil 200 | 0.050 g |
| Aspartame | 0.050 g |
| Caramel powder | 0.100 g |
| Peppermint powder aroma | 0.060 g |

The applicant has investigated this product further and has surprisingly discovered that an anti-HCV activity appears to derive from only one plant, demonstrating both good activity and no detectable cell cytotoxicity. That plant is *Astragalus*, and it has further been determined that a fraction purified by a factor of greater than 10, more particularly greater than 50, more particularly still greater than 75 and most particularly between 75 and 200 is particularly active.

The active fraction can be produced in good yield in effectively a three stage process comprising:
I. an alcoholic extraction (which may be repeated);
II. an ethanol-water precipitation process (which may be repeated); and
III. a systematic solvent fractionation step with a plurality of solvents of different polarity.

Preferably, the systematic solvent fractionation utilizes a number of different solvents commencing with the least polar and finishing with the most polar. The active fraction is a dichloromethane fraction or a solvent with similar polarity.

The active fraction (and sub-fractions) can be characterized with reference to one or more markers, one or a combination of which may be responsible for the anti-HCV activity and polymerase inhibition. Particular markers identified include:
Astragaloside I,
Formononetin-7-O-β-D-glucoside; and
3'-hydroxyl-formononetin-7-O-β-D-glucoside.

Additionally they can be identified by way of TLC fingerprints as set out in the detailed description.

The plant which exhibits the activity is a member of the Leguminosae family, more particularly huang qi:
Pharmaceutical name: Radix Astragali Membranaceous;
Botanical name: *Astragalus membranaceus* (Fisch) Bge. or *Astragalus membranaceus* Bge var. *Mongholicus* Hsiao (hereafter *Astragalus*).

The plant may be referred to as Milkvetch in Europe and it is the root which is used.

In traditional Chinese herbal medicine a dosage (based on dry raw material) of 9-30 g and occasionally up to 60 g is used. Typically it is taken as a decoction. According to Pharmacopoeia of the People's Republic of China (English Edition 2000) Vol I a cold water extraction method gives a water soluable extractive of not less than 17%.

According to Chinese Herbal Medicine, Materia Medica, Revised edition, chemically the root of *Astragalus membranaceus* is known to contain, as major ingredients, D-β asparagine, 2'4'-dihydroxy-5,6-dimethoxyisoflavane, calycosin, formononetin, cycloastragenol, astragalosides, choline, betaine, kumatakenin, sucrose, glucuronic acid and β-sitosterol.

It's chemical constituents are discussed further in Chinese Drugs of Plant Origin, Springer-Verlag which further discusses it's pharmacology and the symptomatic relief in the treatment of chronic hepatitis.

According to Chang H M and But P P (1987) Pharmacology and applications of Chinese Materia Medica (Vol ii) World Scientific Publishing, *Astragalus membranaceus* may enhance immunological function. More particularly reference is made to the use of a 100% decoction, 0.4 ml daily, to "protect" the liver and a clinical trial in which Huangqi injection achieved normalization of GPT levels in 80% of patients. (This is a symptomatic treatment.)

None of the referenced documents or other published literatures teaches the use of a single herb *Astragalus*, or a defined fraction thereof, as an antiviral in the treatment of hepatitis C.

Additional prior art identified includes:
CN1616097 which discloses a lozenge containing attenuated Newcastle disease virus vaccine or deactivated Newcastle disease virus vaccine, 10-120 hemagglutination units, astragalus root 1-20000 mg, liquiritigenin 1-1000 mg, supplementary material and stabilizer. It is stated to be suitable for preventing SARS and other viral infectious respiratory tract diseases and to have auxiliary treatment effects on hepatitis B and C.

CN1607003 which discloses the use of a composition comprising Chinese caterpillar fungus (50-90 parts) with astragalus root (10-50 parts) as an auxiliary therapeutic agent for hepatitis C. It is stated to adjust immune function and improve curative effect.

US2005/0074428 which discloses an adjuvant agent for use in combination with interferon and ribivarin for treating Hepatitis C containing 50-90 wt % cordyceps sinensis and 10-50 wt % astragalus memsrancens.

CN 1448163 which discloses a Chinese recipe comprising astragalus root among some eleven herbs to treat various diseases including hepatitis C.

CN1393255 which discloses a nineteen herb mix including astragalus root for treating hepatitis C.

CN1593586 which discloses a pill for treating hepatitis C comprising at least 15 herbs, one of which is raw astragalus root.

US2005/0147699 which discloses the use of an astragalus radix and codonopsis pilosulae radix mixed extract for inhibiting carcinogenesis and metastasis. It states that *Astragalus* is recorded, in the traditional pharmacopea, to treat chronic nephritis, albuminuria, myositis, antihypertensive, coronary artery disease, cerebral infarction, peptic ulcer (duodenal and gastric ulcer), renal disease and diabetes mellitus. It makes no reference to its potential use as an anti viral agent.

Indeed none of the documents suggests that a single herb *Astragalus* extract can be used alone as an antiviral to treat hepatitis, particularly hepatitis C.

SUMMARY OF THE INVENTION

According to a first aspect of the present invention there is provided a single herb *Astragalus* extract or an active fraction thereof, for use as an antiviral in the treatment of Hepatitis C.

Preferably the active fraction is an extract of *Astragalus* purified by at least a factor of 10 with reference to dried raw plant material, and which is characterized in that it comprises at least one marker selected from the group consisting of:

Astragaloside I;
Formononetin-7-o-β-d-glucoside; and
3'-hydroxyl-formononetin-7-o-β-d-glucoside.
Preferably it comprises all three markers.

In a particularly favored embodiment, the extract is purified by at least a factor of 50, most preferably by a factor of between 75 and 200 and can be characterized by the presence of the three markers identified above. In fact, at least six defined peaks can be identified in this fraction.

In a preferred embodiment the extract is used or formulated as a botanical drug.

In an alternative embodiment the extract may be used as a food, dietary supplement or food additive. The term food includes food or drink and articles used for components of such articles.

The botanical terms used herein are intended to have the meanings as used by the FDA in their directive "Guidance for Industry Botanical Drug Products" (June 2004) which directive is incorporated by reference. It will, however, by understood by persons skilled in the art that in different countries different terminology may be used. Reference to the FDA guidance terminology is used for consistency and should not be taken to be limiting. Thus differing but equivalent terms used by, for example, the EMEA in their Guidelines on Quality of Herbal Medicinal Products/Traditional Herbal Medicinal Products (CHMP/THMP adopted March 2006), will be understood by the skilled person to be encompassed by the terms used herein.

According to a second aspect of the present invention there is provided *Astragalus* raw material packaged or otherwise sold in a manner which indicates it is suitable and intended for use as an antiviral to treat Hepatitis C.

Preferably the raw material is cultivated and harvested from a designated production site under managed agricultural practice.

According to a third aspect of the present invention there is provided the use of *Astragalus* or a single herb extract thereof in the manufacture of a medicament for the antiviral treatment of Hepatitis C.

According to a forth aspect of the present invention there is provided the use of *Astragalus* or a single herb extract thereof in the manufacture of a food, dietary supplement or food additive for the antiviral treatment of Hepatitis C.

According to a fifth aspect of the present invention there is provided a method for producing an extract of *Astragalus* which exhibits anti-HCV activity in a replicon assay, and which is purified by at least a factor of 10 with reference to dried raw plant material, and which is characterized in that it comprises at least one marker selected from the group consisting of:

Astragaloside I;
Formononetin-7-o-β-d-glucoside; and
3'-hydroxyl-formononetin-7-o-β-d-glucoside
comprising:
1) an alcoholic extraction (which may be repeated);
2) an ethanol-water precipitation process (which may be repeated); and
3) a systematic solvent fractionation step with a plurality of solvents of different polarity.

Preferably, the alcoholic extraction is an ethanolic extraction. The ethanolic extraction is preferably conducted under reflux. Most preferably it is repeated. Preferably high concentration ethanol is used (greater than 50% by concentration.)

The alcoholic extraction is followed by an ethanol-water precipitation and the supernatant recovered. The ethanol is recovered leaving a concentrate.

The concentrate is then dissolved in water to give an aqueous solution which is subjected to systematic solvent fractionation using solvents of different polarity. Preferred solvents are: Petroleum ether, dichloromethane, and ethyl acetate.

The active fraction is the dichloromethane extract AS-C.

According to a sixth aspect of the present invention there is provided a method of treating Hepatitis C comprising administering an effective amount of a single herb *Astragalus* extract or an active fraction thereof.

The single herb *Astragalus*, or an active fraction thereof is preferably provided in unit dosage form. Most preferably it is provided in a form suitable for oral delivery e.g. a filled capsule. The skilled person will appreciate other dosage forms may alternatively be presented.

Preferably the extract is used in an amount equivalent to an amount of between 9 and 60 g of dried raw material/day.

In one embodiment the *Astragalus* or an active fraction thereof is administered by way of a combination treatment with at least one other immuno-modulatory or antiviral drug e.g. Interferon and/or Ribavirin.

The drugs may be administered together simultaneously or sequentially.

According to a seventh aspect of the present invention there is provided a botanical drug, food, dietary supplement or food additive comprising an extract of *Astragalus* purified by at least a factor of 10 with reference to dried raw plant material, and which is characterized in that it comprises at least one marker selected from the group consisting of:
Astragaloside I;
Formononetin-7-o-β-d-glucoside; and
3'-hydroxyl-formononetin-7-o-β-d-glucoside.

Figure 4:
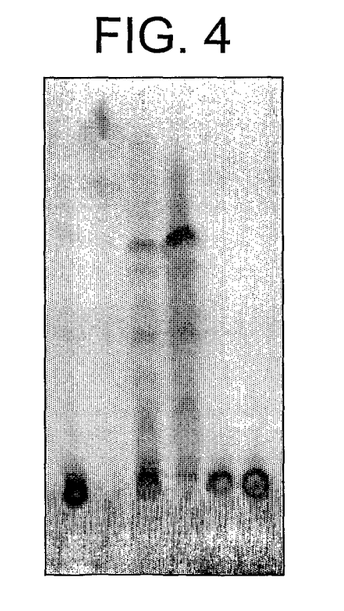
FIG. 4 is a TLC fingerprint of a number of different fractions (UV254 nm)
Figure 5:
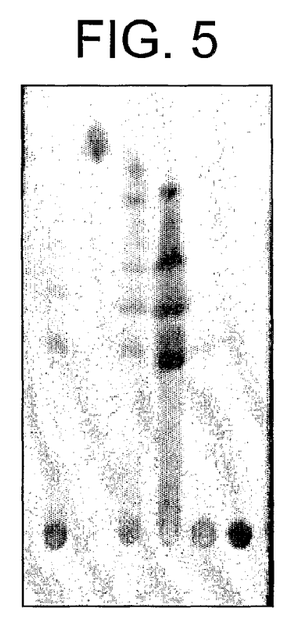
FIG. 5 is a TLC fingerprint of a number of different fractions (UV365 nm)
Figure 6:
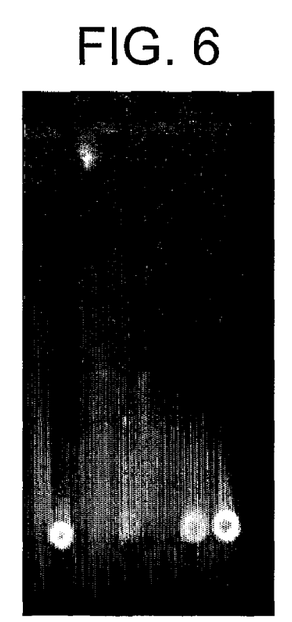
FIG. 6 is a TLC fingerprint of a number of different fractions (daylight)

It may be further characterized by the presence of characteristic spots present by way of a TLC fingerprint as shown in any one of FIGS. 4-6.

The present invention will be further illustrated, by way of Example only, with reference to the following methodology and data in which.

DETAILED DESCRIPTION

Methodology

Example 1

Activity of Component Herbs

Figure 1:
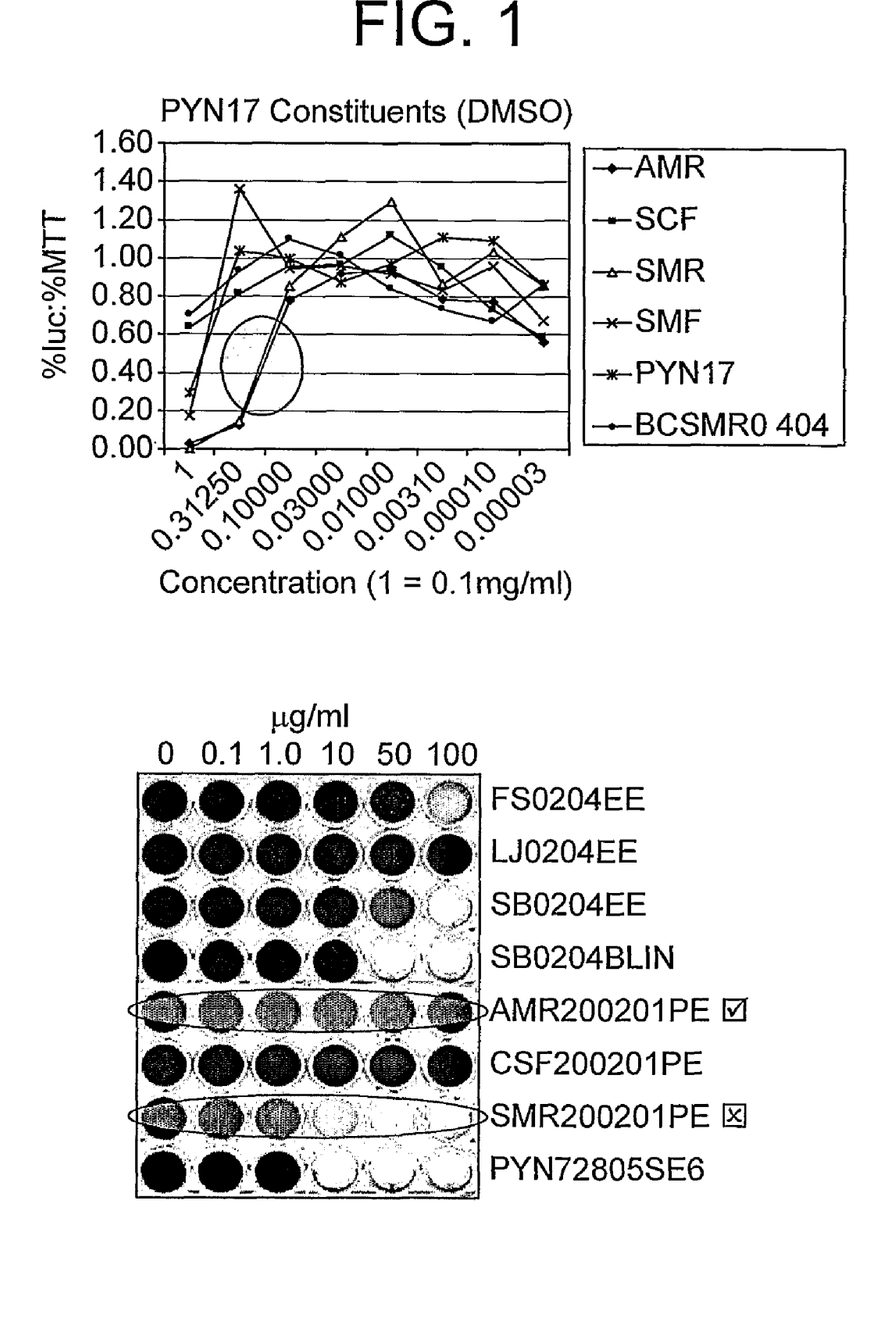
FIG. 1 illustrates the anti-hepatitis C virus activity of both SMA and AMR together with toxicity data.

Following on from the discovery that the four herb combination demonstrated anti hepatitis C activity (by replicon Assay) the Applicant looked at the activity of the individual herbs. FIG. 1 illustrates the activity of the Pyn 17 constituents:
AMR—*Astragalus membranaceus* root;
SCF—*Schisandra chinensis* fruit;
SMR—*Salvia miltiorrhiza* root; and
SMF—*Silybum marianum* fruit
compared to the controls:
PYN17—four herb combination (positive control); and
BCSMRO404—no plant extracts (negative control).

Both AMR and SMR appear to demonstrate inhibitory activity in the HCV replicon assay. This is particularly evident at high concentrations, as shown in the left hand panel of FIG. 1. The right hand panel of FIG. 1 shows cytotoxicity data in the same replicon cells. This indicates that AMR displays no observable cell cytotoxicity whereas SMR is cytotoxic at high concentrations.

Having determined that the *Astragalus membranaceus* demonstrated activity and a lack of toxicity they sought to identify specific active fractions.

Example 2

*Astragalus* Root Extraction Process

Root material was dried in an oven at 60° C. for 3 hours, pulverised into a coarse powder and passed through a sieve (10 mesh). It was then subjected to an alcoholic extraction as set out in FIG. 2.

Figure 2:
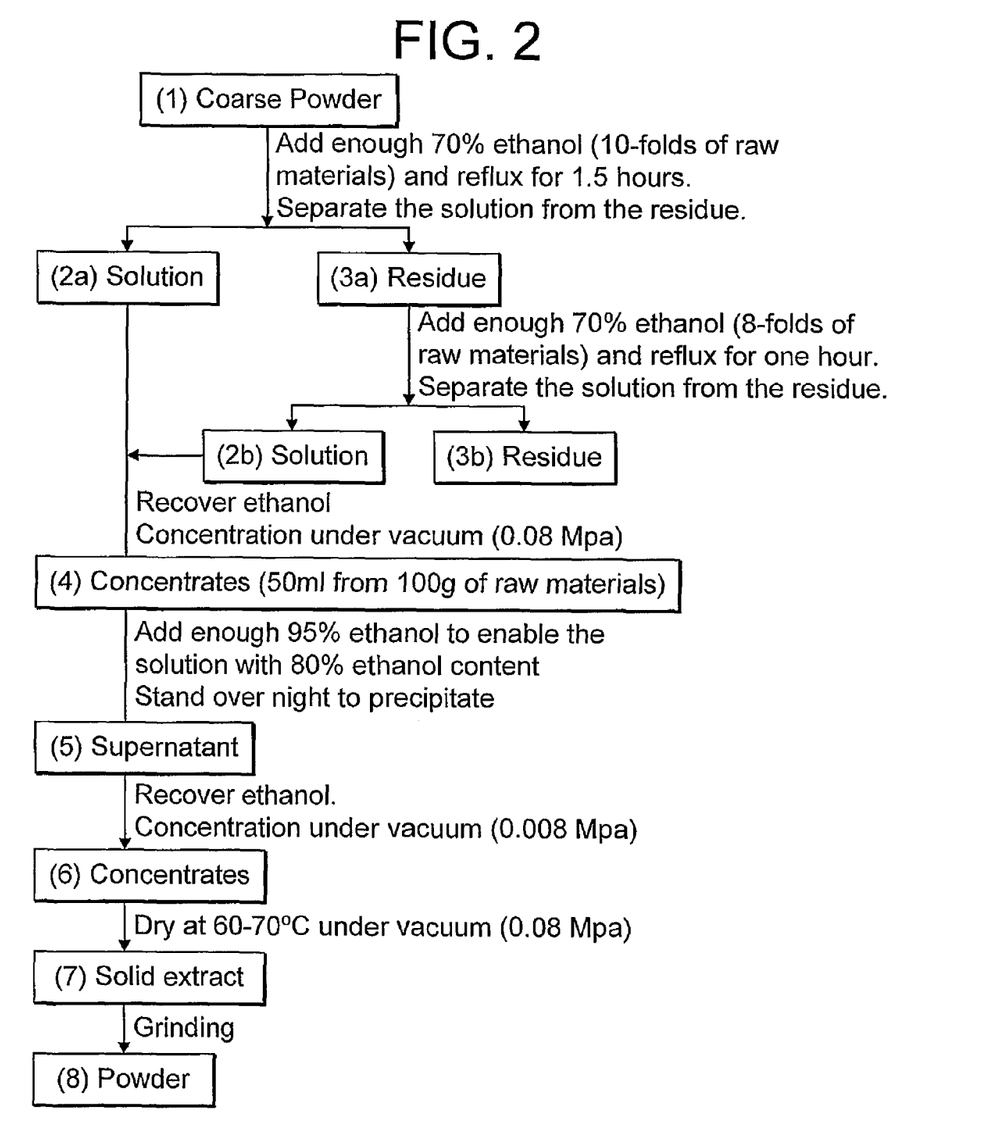
FIG. 2 is a flow diagram of an alcoholic extraction process giving rise to a primary extract containing less than 15% by weight of the starting raw material.

Briefly this comprised the following steps:
1. To 100 g of coarse powdered *Astragalus membranaceus* (1) was added 70% ethanol (10 folds of raw material). This was then refluxed for 1.5 hours and the solution (2a) separated from the residue (3a);
2. To the residue was added 70% ethanol (8 folds of raw material). This was then refluxed for 1 hour and again the solution (2b) was separated from the residue (3b);
3. The solutions (2a and 2b) were combined, and the ethanol recovered under vacuum at a pressure of 0.08 MPa to give 50 ml of a concentrate (4);
4. To the concentrate was added 95% ethanol. The solution was allowed to stand over night and the precipitate separated from the supernatant (5) by filtration;
5. Again the ethanol was recovered under vacuum at a pressure of 0.08 MPa and a concentrate (6) obtained;
6. The concentrate was dried at 60-70° C. under vacuum at a pressure of 0.08 MPa to give a solid extract (7).
7. The solid extract was then ground to a powder (8). This powdered primary extract had a solid yield of between 11.7 and 13% by weight compared to the dry weight of starting material. i.e. It had been purified by a factor of about 8.

The content of Astragaloside IV, the standard chemical marker for *Astragalus* was greater than 0.4%.

Example 3

Figure 3:
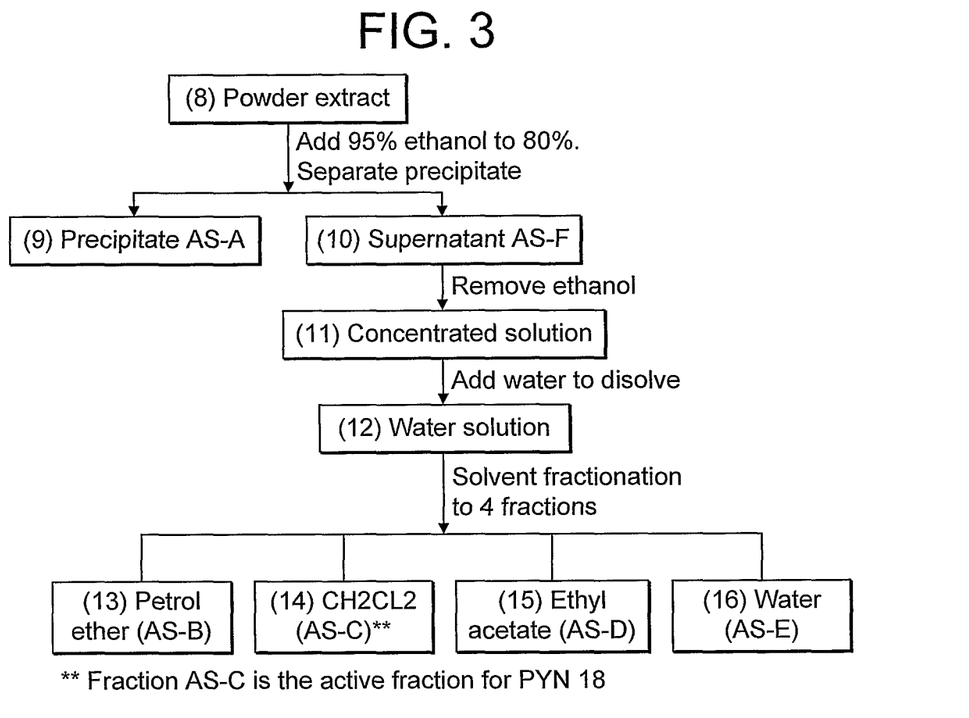
FIG. 3 is a flow diagram showing the fractionation of the primary extract to give a more concentrated active fraction or secondary extract.

The primary extract obtained by the method illustrated in FIG. 2 was fractionated as set out in FIG. 3.

Briefly this comprised the following steps:
1. To the primary extract (8) was added 95% ethanol to 80% and this was again allowed to stand over night. The precipitate (9) "AS-F" was separated from the supernatant (10) "AS-A" by filtration;
2. The ethanol was recovered under vacuum at a pressure of 0.08 MPa and a concentrated solution (11) obtained;
3. Water was added to the concentrated solution (11) to form a water solution (12) which was successively partitioned with:
    a. Petroleum ether to give a fraction (13) "AS-B";
    b. Dichloromethane to give a fraction (14) "AS-C"; and
    c. Ethyl acetate to give a fraction (15) "AS-D"; together with
    d. The Water faction (16) "AS-E".

The fractions (9), (10), (13), (14), (15) and (16) were subjected to further activity tests as set out in Table 1 below:

TABLE 1

| Sample codes | Source | Total weight (g) | Starch (%) | Fraction Yield (%) |
|---|---|---|---|---|
| AS-F (9) | 80% ethanol soluble fraction | 4.0 | 25 | 12.4 |
| AS-B (13) | petroleum ether fraction | 2.0 | 0 | 0.21 |
| AS-C (14) | methylene dichloride fraction | 10.5 | 0 | 1.1 |
| AS-D (15) | ethyl acetate fraction | 1.1 | 0 | 0.12 |
| AS-E (16) | aqueous fraction | 100.0 | 0 | 10.5 |
| AS-A (10) | precipitates | 129.0 | 0 | 12.9 |

FIGS. 4-6 are TLC plates showing from left to right, fractions (9), (10), (13), (14), (15), and (16). The TLC plates are silica gels and the developing system was chloroform/methanol/water (8:2:0.2).

FIG. 4 shows detection with UV at 254 nm;

FIG. 5 shows detection with UV at 365 nm;

FIG. 6 is observed in daylight following treatment with 10% sulphuric acid in ethanol followed by heating.

Fraction (14) shows a plurality of distinct spots. At least 6 are clearly seen at 254 nm Fraction 14 AS-C was found to be particularly active in the replicon assay (Example 4 Table 5). It had a solid yield of about 1.1% by weight compared to the dry weight of starting material. In fact it had been purified by a factor of about 90%.

This fraction had a chromatographic profile as illustrated in FIGS. 4-6.

Example 4

In order to test the activity of the fractions ASA to ASF__10 mg of each sample was dissolved in 1 ml of DMSO and sonicated for 15 minutes. Two additional samples PA (crude *Astragalus* extract as WO2005079823) and INFα (standard treatment) were run as comparators. The solubility of the samples is shown in Table 2 below:

TABLE 2

| Sample No. | Sample name | Solubility |
|---|---|---|
| 1 | PA 0705 | Didn't all dissolve in DMSO |
| 2 | ASA 0705 | All dissolved |
| 3 | ASB 0705 | Dissolved in DMSO, fine precipitate formed when diluted further in medium |
| 4 | ASC 0705 | All dissolved |
| 5 | ASD 0705 | All dissolved |
| 6 | ASE 0705 | All dissolved |
| 7 | ASF 0705 | All dissolved |
| 8 | IFN alpha | |

The DMSO solutions were then diluted 1/10 in tissue culture medium and filtered. This concentration was called NEAT. 10 μl per well was used, total volume in the test well 100 μl. All concentrations set up as 5 replicates. 3 replicates of the same dilutions of the DMSO.

The dilutions of the extract samples are shown in Table 3 below and those for IFNα are shown in Table 4.

TABLE 3

| Dilutions | Final conc/ml in μg |
|---|---|
| NEAT | 100 |
| 1/2 | 50 |
| 1/4 | 25 |
| 1/8 | 12.5 |
| 1/10 | 10 |
| 1/25 | 4 |
| 1/50 | 2 |
| 1/100 | 1 |

TABLE 4

| Final conc in IU/ml | Final conc in pg/ml |
|---|---|
| 200 | 1000 |
| 100 | 500 |
| 50 | 250 |
| 10 | 50 |
| 5 | 25 |
| 2.5 | 12.5 |
| 1 | 5 |
| 0.5 | 2.5 |

In the first assay the replicon cells were plated out at a concentration of $5 \times 10^3$/well in 90 μl. The following day the test samples were added in 10 μl. The plates were incubated for a further 72 hours and harvested and assayed using the Dual Luciferase Assay Promega. The replicon cell line expresses Renilla luciferase.

The samples were tested for cytotoxicity by setting up a separate 96 well plate with each sample and concentration in duplicate. The cells were labeled with tritiated thymidine for 24 hours and harvested.

For the second assay a separate plate with the top 5 concentrations was set up and labeled for 2 hours with wst-1 (Roche) and the OD read at 450 nm and 630 nm. Wst-1 is a viable cell stain.

Results

Assay 1: Mean of Reading from Cells without any Drug Added 198906.

The results are shown in Table 5.

TABLE 5

| Conc ug/ml | PA 0705 | ASA 0705 | ASB 0705 | ASC 0705 | ASD 0705 | ASE 0705 | ASF 0705 | Conc pg/ml | IFN alpha |
|---|---|---|---|---|---|---|---|---|---|
| 100 | 6 | 0 | 77 | 98.2 | 60.5 | 0 | 46 | 1000 | 85 |
| 50 | | 0 | 0 | 98 | 0 | 0 | 0 | 500 | 67.5 |
| 25 | | | 0 | 97 | 0 | 0 | 0 | 250 | 46.1 |
| 12.5 | | | 1 | 91.6 | 0 | 0 | 0 | 50 | 26 |
| 10 | | | | 52 | 0 | 0 | 0 | 25 | 22 |
| 4 | | | | | | | | 12.5 | |
| 2 | | | | | | | | 5 | |

The readings obtained with no added drug were quite high.

The result obtained with the interferon at these concentrations is typical of this assay.

It seemed from these results that inhibition was obtained with some of the samples at the higher concentrations so the assay was repeated.

Assay 2.

The results are shown in Table 6.

TABLE 6

Mean of reading from cells with no drug added. 71676.
% inhibition of expression of *Renilla* luciferase

| Conc ug/ml | PA 0705 | ASA 0705 | ASB 0705 | ASC 0705 | ASD 0705 | ASE 0705 | ASF 0705 | Conc pg/ml | IFN alpha |
|---|---|---|---|---|---|---|---|---|---|
| 100 | 7 | 64.1 | 58 | 99 | 79 | 36 | 89 | 1000 | 98 |
| 50 | 0 | 00 | 0 | 98.8 | 0 | 0 | 12 | 500 | 95 |
| 25 | 0 | 0 | 0 | 96 | 0 | 0 | 19 | 250 | 981 |
| 12.5 | 0 | 0 | 0 | 73 | 0 | 0 | 30 | 50 | 70 |
| 10 | 0 | 0 | 0 | 71.2 | 0 | 0 | 38 | 25 | 64 |
| 4 | 0 | 0 | 0 | 46.6 | 0 | 0 | 35 | 12.5 | 45 |
| 2 | 0 | 0 | 0 | 40.6 | 0 | 0 |  | 5 | 58 |
| 1 | 0 | 0 | 0 | 15.4 | 0 | 0 |  |  |  |

The dilutions were tested for cytotoxicity in the wst-1 assay and this plate was also examined under the microscope. This assay will not detect cytostatic agents.

Sample 4 killed the cells at the top 2 dilutions; they looked less healthy at the 3$^{rd}$ concentration. All the other samples had cells that were healthy in appearance. This is reflected in the wst-1 results.

Assay 2 wst-1 Results.

The results are shown in Table 7

TABLE 7

Mean OD reading at 450 nm

| Conc ug/ml | Sample 1 | Sample 2 | Sample 3 | Sample 4 | Sample 5 | Sample 6 | Sample 7 | Conc pg/ml | IFN alpha |
|---|---|---|---|---|---|---|---|---|---|
| 100 | 0.443 | 0.522 | 0.802 | 0.306 | 0.713 | 0.520 | 0.619 | 1000 | 0.728 |
| 50 | 0.455 | 0.546 | 0.836 | 0.445 | 0.839 | 0.736 | 0.821 | 500 | 0.740 |
| 25 | 0.585 | 0.532 | 0.756 | 0.683 | 0.750 | 0.875 | 0.590 | 250 | 0.650 |
| 12.5 | 0.561 | 0.507 | 0.539 | 0.602 | 0.567 | 1.020 | 0.967 | 50 | 0.772 |
| 10 | 0.542 | 0.747 | 0.507 | 0.884 | 0.705 | 0.888 | 0.887 | 25 | 0.527 |

It should be noted that the IFN alpha concentrations are pg/ml.

Figure 7:
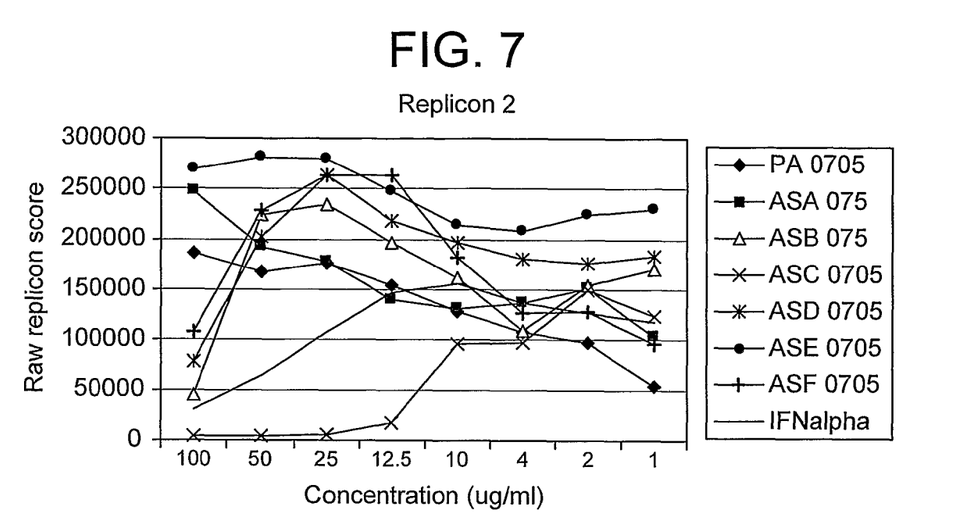
FIG. 7 is a graph showing the activity of various fractions in a replicon assay.
Figure 8:
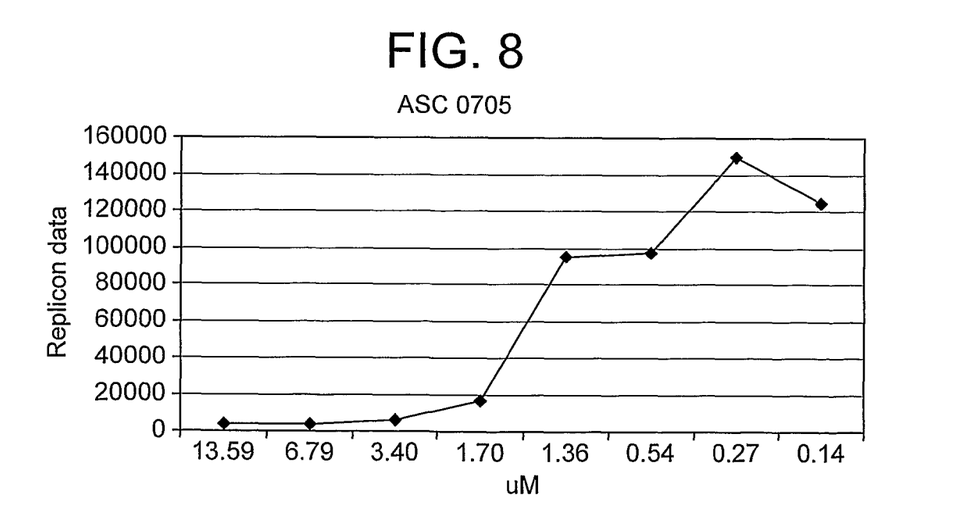
FIG. 8 is a graph showing the activity of ASC 705 (14) at different concentrations.

The results are illustrated graphically in FIGS. 7 and 8.

FIG. 7 shows the raw replicon scores of the samples against concentration. ASC-0705 is clearly the best performer and outperforms IFN alpha (standard treatment). It also demonstrates that the best activity is at a concentration above 10 ug/ml.

FIG. 8 shows activity against concentration. Clearly the optimum concentration is above about 1.36 uM Example 5

Figure 9:
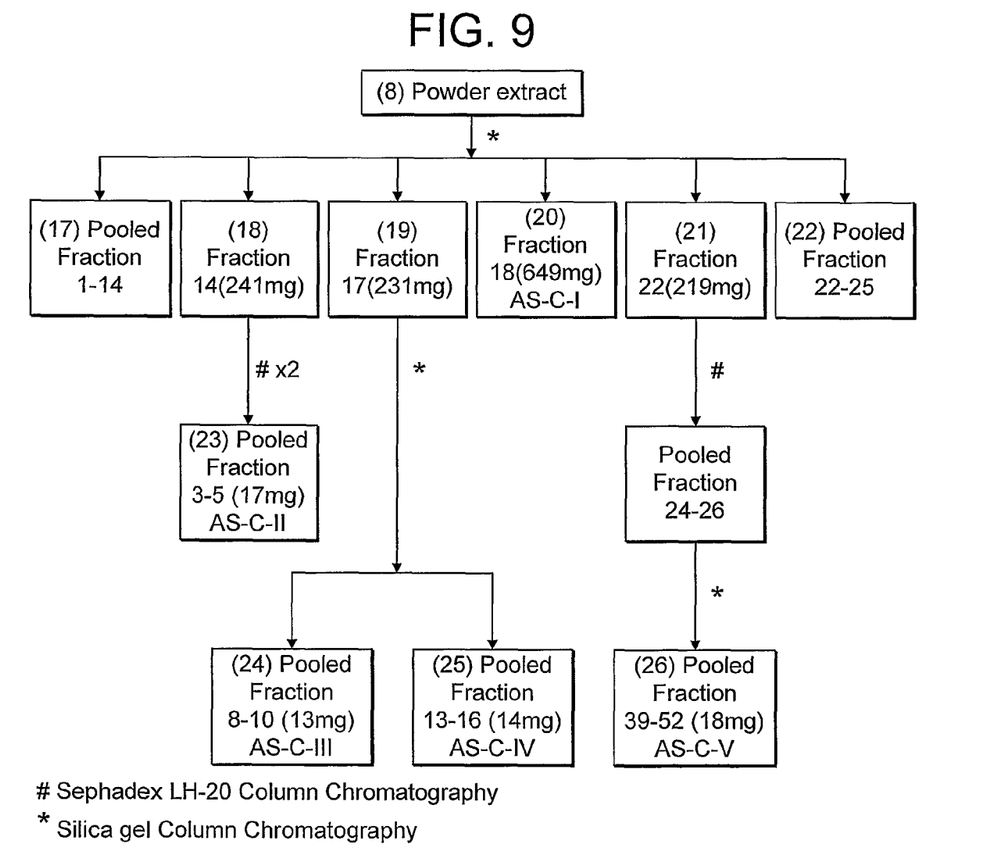
FIG. 9 is a flow diagram showing the further fractionation of the secondary extract.

The fraction (14 AS-C) was subjected to a chromatographic separation step as illustrated in FIG. 9 and as set out below. Briefly this comprised the following steps:
1. 6.2 g of the Dichloromethane extract (14) "AS-C" from *Astragalus* root was separated by silica gel column chromatography and eluted in gradient elution with chloroform, chloroform/methanol (100:5), chloroform/methanol (100:10), chloroform/methanol (100:15), and methanol and 25 fractions obtained which were initially split into six pools (17; 18; 19; 20; 21 and 22);
2. Pooled fractions 1-14 (17) contained no significant chemicals;
3. Fraction 15 (18) had a weight of 241 mg and was further purified twice with Sephadex column chromatography and eluted with methanol to get a fraction (23) "AS-C-II" which was shown to be active BUT which also exhibited toxicity;
4. Fraction 17 (19) had a weight of 231 mg and was further separated into two fractions by way of silica gel column chromatography eluting with chloroform/methanol (94:6). The two fractions weighed 13 mg, fraction (24) "AS-C-III" and a 14 mg (25) "AS-C-IV";
5. The 18$^{th}$ fraction (20) was left to stand and 649 mg of a white powder precipitated as AS-C-I. This was found to exhibit activity with no toxicity;
6. The 22$^{nd}$ fraction (21) weighing 219 mg was separated by Sephadex column and Silica column to obtain an 18 mg fraction (26) "AS-C-V".

The extracts which were tested are identified in Table 8 below:

TABLE 8

| Ref | Sample | Source | Total weight | % content with reference to dry raw material | Factorial change from raw material |
|---|---|---|---|---|---|
| (14) | AS-C |  | 6.2 g | 0.79671%* | 125 |
| (20) | AS-C-I | AS-C 18$^{th}$ fraction eluted | 649 mg | 0.08339% | 1,199 |

TABLE 8-continued

| Ref | Sample | Source | Total weight | % content with reference to dry raw material | Factorial change from raw material |
|---|---|---|---|---|---|
| (23) | AS-C-II | AS-C 15$^{th}$ fraction eluted | 17 mg | 0.00218% | 45,871 |
| (24) | AS-C-III | AS-C 17$^{th}$ fraction eluted | 13 mg | 0.00167% | 59,880 |
| (25) | AS-C-IV | AS-C 17$^{th}$ fraction eluted | 14 mg | 0.00179% | 55,865 |
| (26) | AS-C-V | AS-C 22$^{nd}$ fraction eluted | 18 mg | 0.00231% | 43,290 |

Figure 10:
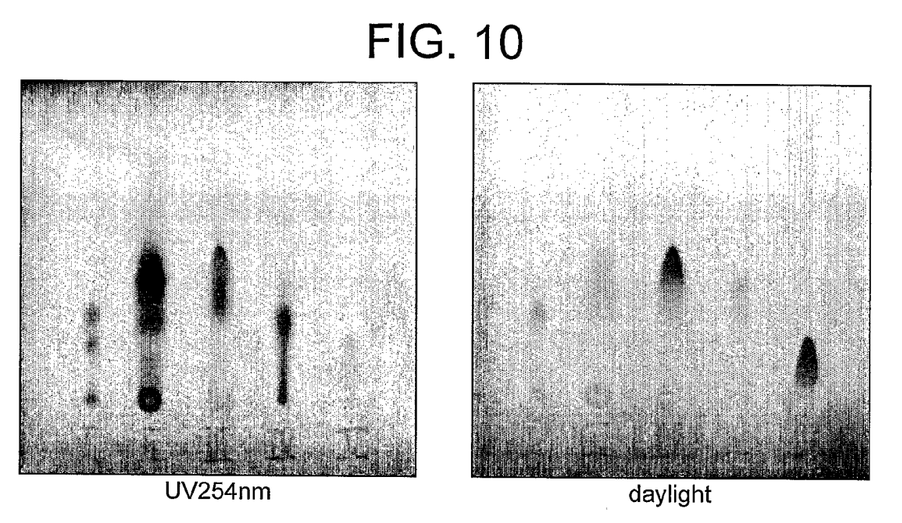
FIG. 10 is a TLC fingerprint of the five fractions AS-C-I to AS-C-V in chloroform/methanol 9:1
Figure 11:
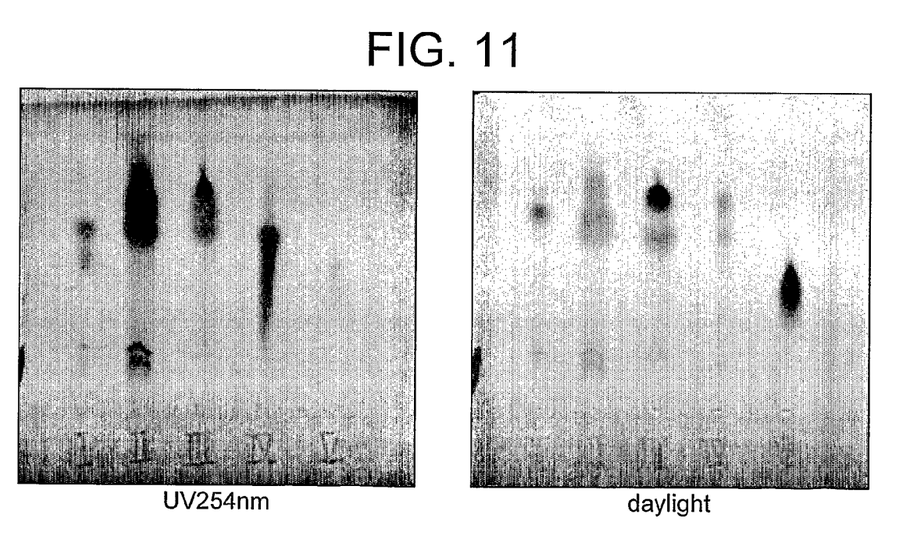
FIG. 11 is a TLC fingerprint of the five fractions AS-C-I to AS-C-V in chloroform/methanol/water 8:2:02

*Calculated on basis that 100 g of primary extract (8) contains 12.85% of the starting material and accordingly the equivalent weight of dry raw material is 778.2 g Each of the five referenced sub fraction samples was subjected to analysis by TLC and the results are illustrated in FIGS. 10 and 11.

FIG. 10 shows silica gel plates developed in chloroform/methanol (9:1). The left hand plates is viewed under UV at 254 nm and the right hand plate under daylight (spray with 10% sulphuric acid in ethanol and then heat the plate until the spots are clearly seen).

FIG. 11 shows silica gel plates developed in chloroform/methanol/water (8:2:0.2). The left hand plates is viewed under UV at 254 nm and the right hand plate under daylight (spray with 10% sulphuric acid in ethanol and then heat the plate until the spots are clearly seen).

In both cases the samples read from left to right: AS-C-I; AS-C-II; AS-C-Ill; AS-C-IV; AS-C-V.

Example 6

Each of six samples: "AS-C"; "AS-C-I"; "AS-C-II"; "AS-C-III"; "AS-C-IV"; and "AS-C-V" were dissolved in DMSO to give a 10 mg/ml stock solution. The samples were:
1. analysed for purity and identity; and
2. tested for anti HCV activity.

1. Purity and Identity

The six samples, AS-C, AS-C-I, AS-C-II, AS-C-III, AS-C-IV, AS-C-V were analysed with respect to purity and identity using LC-UV and LC-MS. The analysis gave the following data AS-C fraction contained several (>6) small peaks (m/z 269, 301, 303, etc.)
AS-C-I two main peaks (m/z 269, 301)
AS-C-II one peak (m/z 301)
AS-C-III one peak (m/z 303)
AS-C-IV one peak (m/z 269)
AS-C-V no peaks As at this stage, the components corresponding to the peaks had not been identified so the only estimation that could be done was to compare the peak areas with the DMSO peak area:
I. "AS-C-II" and "AS-C-IV" contained a single peak which is higher than the DMSO peaks.
II. "AS-C" and "AS-C-I" are mixtures;
III. "AS-C-III" contains a single peak which is lower than the DMSO peak.
IV. "AS-C-V" does not contain any peak visible in UV.

It should be noted that the purity was analysed with UV detection and any compounds that do not absorb in UV will not be detected. Material from the peaks was analysed with MS to determine the m/z (given above).

2. Anti-HCV Activity

The samples were tested for anti-HCV activity in:
a) a replicon assay (Reblikon),
b) a NS5B assay and
c) a NS3/NS4A full length protease assay.

To estimate the selectivity of any "hit" in the replicon assay, the samples were also tested for cytotoxicity in Huh7 cells.

The results are illustrated in Table 9 below which additionally includes purity, peak area and identity data.

TABLE 9

| FRACTION TEST | AS-C | AS-C-I | AS-C-II | AS-C-III | AS-C-IV | AS-C-V |
|---|---|---|---|---|---|---|
| a) REPLICON, EC50 (µg/ml) | 3.7 | 36 | 17 | >50 | >50 | >50 |
| b) NS5B, EC50 (µg/ml) | 9.2 | 24 | >100 | 17 | 19 | >100 |
| c1) NS3/NS4, % inh@100 µg/ml | 95 | 42 | 41 | 45 | 46 | 4 |
| c2) NS3/NS4, % inh@10 µg/ml | 12 | 12 | 25 | 19 | 27 | 37 |
| d) Huh7, CC50 (µg/ml) | >100 | >100 | 60 | >100 | >100 | >100 |
| Purity (LC-UV) | >6 small peaks | 2 peaks | 99% | 97% | 98% | no peaks detected |
| Peak area | 390756 (2.6 min) | 1109851 (2.57 min) | 7887679 (2.63 min) | 2339866 (2.67 min) | 11689463 (2.57 min) | |
| Identity (LC-MS) | m/z 269, 301, 303 etc. | m/z 269 | m/z 301 | m/z 303 | m/z 269 | — |

From the table the following can be determined:
Sample, "AS-C" (Mixture)
a) Inhibits HCV replication in replicon cells showing $EC_{50}=3.7$ µg/ml;
b) Inhibits NS5B at 9.2 µg/ml; m
c) Gives 95% inhibition at 100 µg/ml in the NS3/NS4 assay.
d) Shows no cytotoxicity in concentrations up to 100 µg/ml.

AS-C-I and AS-C-II
a) also show some activity in the replicon assay but at higher concentrations. The determined $EC_{50}$ values were 36 and 17 µg/ml respectively Example 7

In order to further characterise the "AS-C" fraction (14) which exhibited the strongest activity, reference was made to fraction "AS-C-I" (20) as this also exhibited activity and thus it was concluded it contained one or more of the actives responsible for the activity which could serve as markers.

Figure 12:
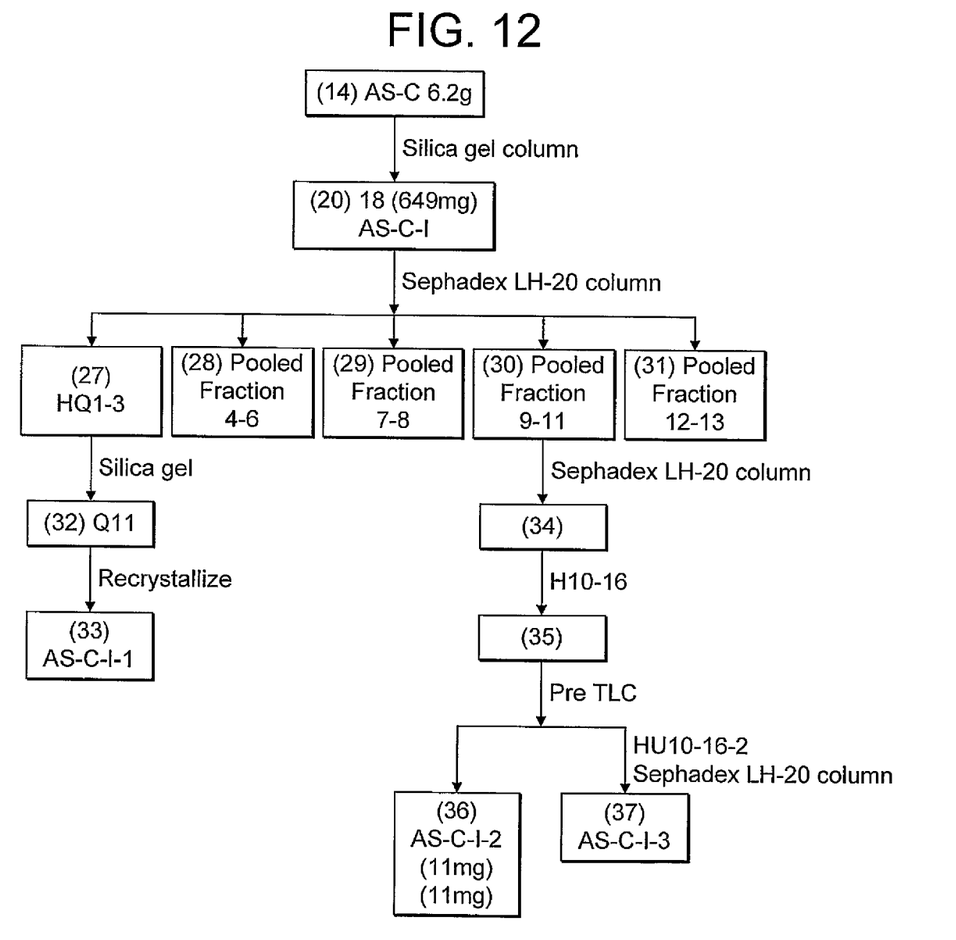
FIG. 12 is a flow diagram showing the isolation, purification and chemical identification of the components present in different AS-C-I sub fractions
Figure 13:
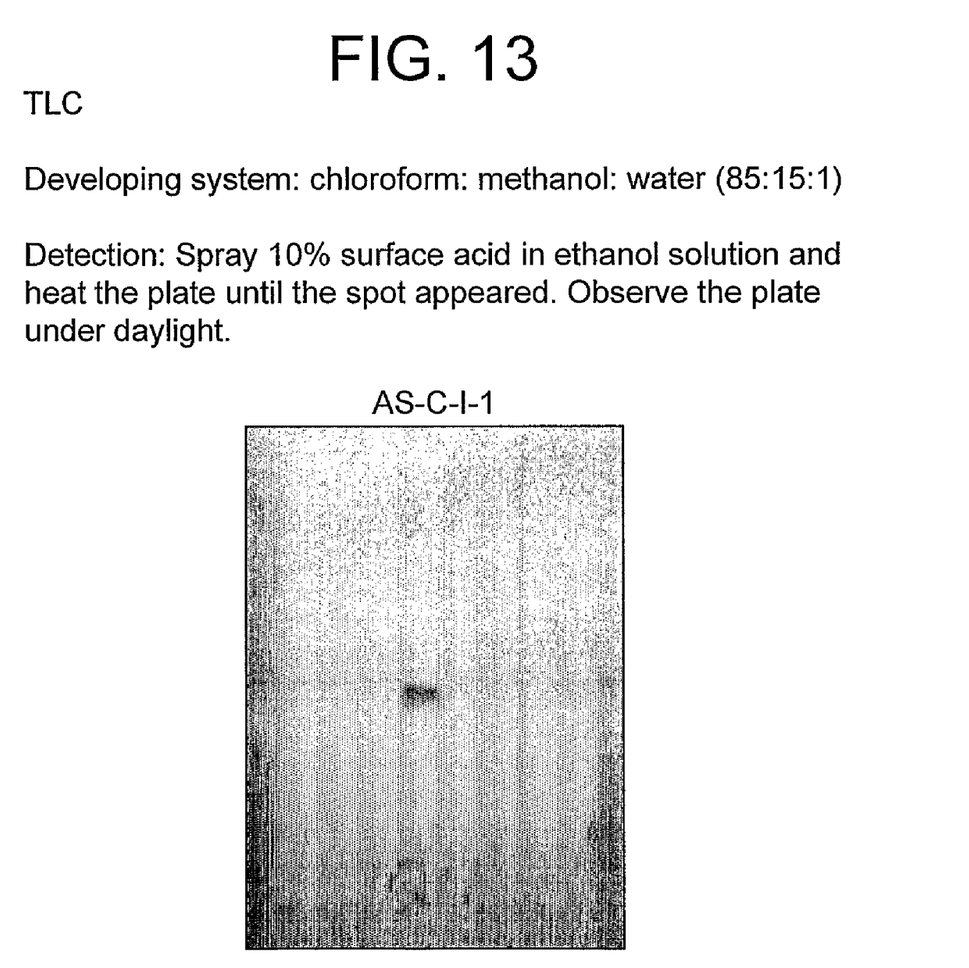
FIG. 13 is a TLC fingerprint of "ASC-I-1" in chloroform: ethanol:water 85:15:1.
Figure 14:
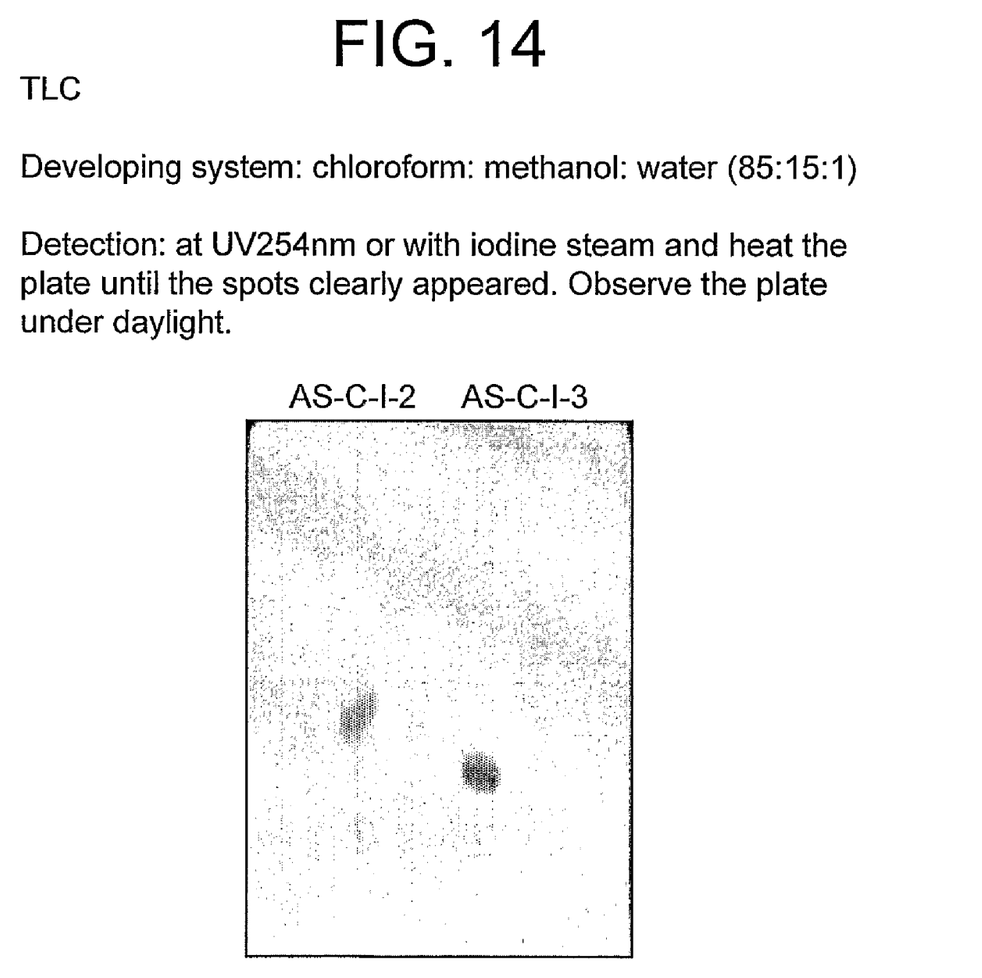
FIG. 14 is a TLC fingerprint of "ASC-I-2" and "ASC-I-3" in chloroform:ethanol:and water 85:15:1 (UV 254 nm)
Figure 15:
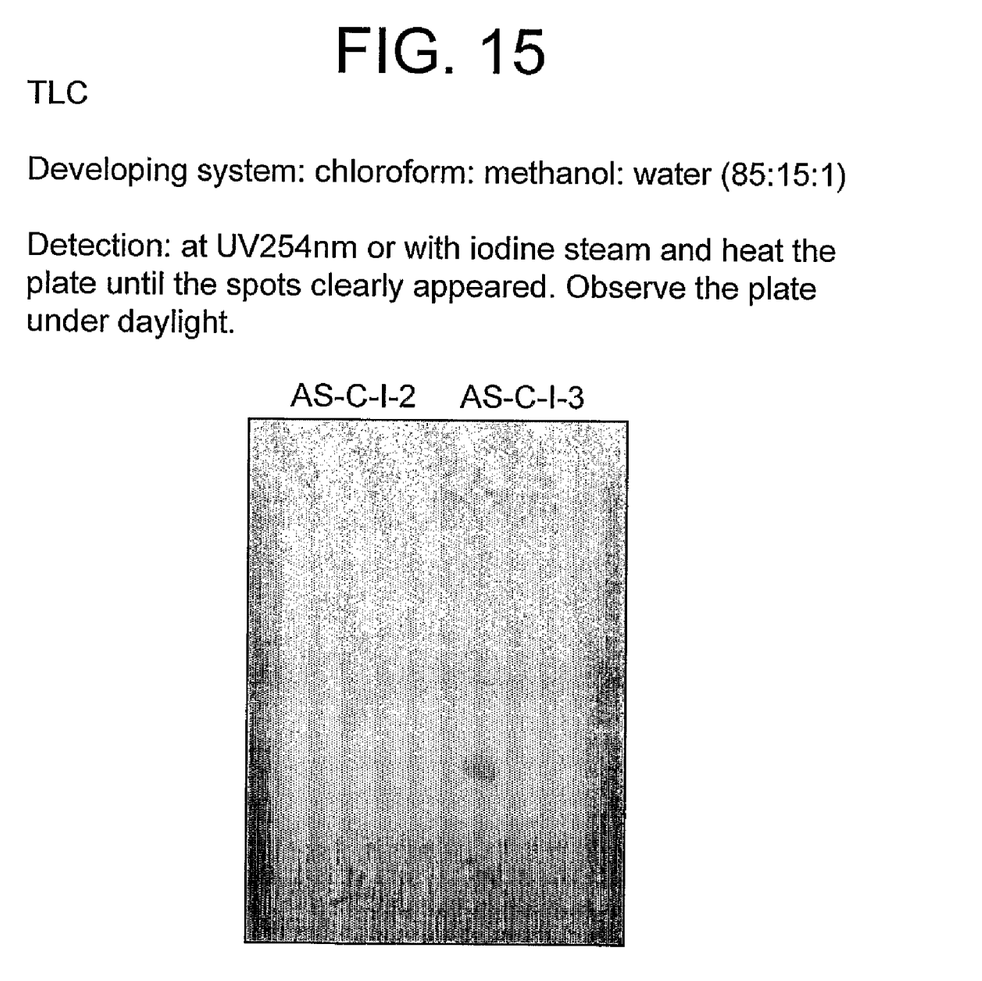
FIG. 15 is a TLC fingerprint of "ASC-I-2" and "ASC-I-3" in chloroform:ethanol:water 85:15:1 (iodine).

Accordingly, and with reference to FIG. 12, the following protocol was followed:
1. 6.2 g of (14) AS-C was separated by silica gel column chromatography and eluted with chloroform/methanol (100:15). The precipitated white powder from the 18th fraction (20) was referred as "AS-C-1" (649 mg).
2. The ASC-1 (20) was dissolved in methanol with supersonication, and then filtrated. The filtrate was separated by Sephadex LH-20 column to obtain three major compounds as showed in the TLC plates illustrated in FIGS. 13-15.
3. Pooled fractions 4-6 (28) showed a spot when sprayed with sulphuric acid and heated;
4. Pooled fractions 9-11 (30) showed 2 spots when the plate was placed in an iodine steam and observed at $UV254_{nm}$ 5. Pooled fractions 4-6 (28) had trace amounts of pigment after purifying by Silica gel column and eluted with chloroform/methanol: 9:1 (32)
6. This sample (32) was dissolved in acetone, refrigerated and re-crystallized to obtain "AS-C-1-1" (33).
7. Pooled fractions 9-11 (30) showed fluorescent spots when purified by a gel column (34), and then TLC method (35). The two fluorescent bands were separated. The band with a higher Rf value was eluted to obtain "AS-C-I-2" (36); while the one with a lower Rf value was purified by Sephadex LH-20 to obtain "AS-C-I-3" (37).

The three compounds identified were analyzed by mass spectrum and nuclear magnetic resonance spectroscopy, respectively. The structures of the three compounds were identified by comparing the data obtained with the existing literature on chemical structures and are shown in Table 10.

TABLE 10

| Sample No. | Spectra tested | Structural analysing results |
|---|---|---|
| AS-C-I-1 | ESI, $^1$HNMR, $^{13}$CNMR, COSY, HMQC, HMBC | Astragaloside I |
| AS-C-I-2 | ESI, $^1$HNMR, $^{13}$CNMR, COSY, HMQC, HMBC | Formononetin-7-O-β-D-glucoside |
| AS-C-I-3 | ESI, $^1$HNMR, HMQC, HMBC | 3'-hydroxyl-formononetin-7-O-β-D-glucoside |

These compounds have the following structures:

Formula 1 Astragaloside I (AS-C-I-1)

R1 = R2 = AC, R3 = Glc

Formula 2: Formononetin-7-O-β-D-glucoside (AS-C-I-2)

Formula 3: 3'-hydroxyl-formononetin-7-O-β-D-glucoside (AS-C-I-3)

The invention claimed is:

1. A method of treating hepatitis C, consisting essentially of administering to a subject having hepatitis C a therapeutically amount of an extract of *Astragalus membranaceus*.

2. The method as recited in claim 1, wherein the *Astragalus membranaceus* extract is purified by at least a factor of 10 compared to the native *Astragalus membraneus*, and which is characterized in that it comprises at least one marker selected from the group consisting of:
   Astragaloside I;
   Formononetin-7-o-β-d-glucoside; and
   3'-hydroxyl-formononetin-7-o-β-d-glucoside.

3. The method as recited in claim 2, wherein the extract of *Astragalus membranaceus* is purified by a factor of 50 compared to the native *Astragalus membranaceus*.

4. The method as recited in claim 3, wherein the extract of *Astragalus membranaceous* is purified by a factor of between 75 and 200 compared to the native *Astragalus membranaceus*.

5. The method as recited in claim 1, wherein the *Astragalus membranaceous* extract is an alcoholic extract.

6. The method as recited in claim 1, wherein the *Astragalus membranaceous* extract has been subjected to an ethanol-water precipitation process.

7. The method as recited in claim 1, wherein the *Astragalus membranaceous* extract has been subjected to a systematic solvent fractionation step with a plurality of solvents of different polarity.

8. The method as recited in claim 7 wherein the *Astragalus membranaceous* extract is obtained from a dichloromethane fractionation or a solvent of similar polarity.

9. The method as recited in claim 1, wherein the *Astragalus membranaceous* extract is *Astragalus membranaceus* (Fisch) Bge, or *Astragalus membranaceus* Bge var. *Mongholicus* Hsiao.

* * * * *

UNITED STATES PATENT AND TRADEMARK OFFICE
CERTIFICATE OF CORRECTION

PATENT NO. : 8,221,801 B2
APPLICATION NO. : 12/304893
DATED : July 17, 2012
INVENTOR(S) : Shouming Zhong et al.

It is certified that error appears in the above-identified patent and that said Letters Patent is hereby corrected as shown below:

In the Claims

Column 14, Line 34 "membranaceous" should be --membranaceus--.
Column 14, Line 38 "membranaceous" should be --membranaceus--.
Column 14, Line 40 "membranaceous" should be --membranaceus--.
Column 14, Line 43 "membranaceous" should be --membranaceus--.
Column 14, Line 47 "membranaceous" should be --membranaceus--.
Column 14, Line 50 "membranaceous" should be --membranaceus--.

Signed and Sealed this
Twenty-fourth Day of March, 2015

Michelle K. Lee
*Director of the United States Patent and Trademark Office*